(12) United States Patent
Williams et al.

(10) Patent No.: US 12,137,955 B2
(45) Date of Patent: *Nov. 12, 2024

(54) BONE CEMENT MIXER

(71) Applicant: Zavation Medical Products, LLC, Flowood, MS (US)

(72) Inventors: Colby Williams, Brandon, MS (US); John Franklin Cummins, Kosciusko, MS (US); John Lawrence Walker, Madison, MS (US); Brad Risher, Brandon, MS (US); Christopher Strahm, Deforest, WI (US); Talya Mathein, Libertyville, IL (US)

(73) Assignee: ZAVATION MEDICAL PRODUCTS, LLC, Flowood, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/357,887

(22) Filed: Jul. 24, 2023

(65) Prior Publication Data

US 2024/0024007 A1 Jan. 25, 2024

Related U.S. Application Data

(63) Continuation of application No. 17/872,785, filed on Jul. 25, 2022, now Pat. No. 11,737,802.

(51) Int. Cl.
*A61B 17/88* (2006.01)
*A61B 17/56* (2006.01)

(52) U.S. Cl.
CPC .... *A61B 17/8833* (2013.01); *A61B 2017/564* (2013.01); *A61B 2017/8838* (2013.01)

(58) Field of Classification Search
CPC ........ A61B 17/8833; A61B 2017/8838; A61B 17/8838
See application file for complete search history.

(56) References Cited

U.S. PATENT DOCUMENTS

| | | | | |
|---|---|---|---|---|
| 5,071,040 A | * | 12/1991 | Laptewicz, Jr. | .... B01F 33/5011 604/218 |
| 5,876,116 A | * | 3/1999 | Barker | ................ B01F 33/5011 366/195 |
| 7,744,270 B2 | * | 6/2010 | Plishka | ............. B01F 33/50112 366/195 |
| 8,303,599 B2 | * | 11/2012 | Hess | .................. A61B 17/8833 606/92 |

* cited by examiner

*Primary Examiner* — Nicholas W Woodall
(74) *Attorney, Agent, or Firm* — IP & T GROUP LLP

(57) ABSTRACT

A bone cement mixing and dispensing system and method for mixing and delivering bone cement therefrom. The system has a mixing container for holding a bone cement mixture, the mixing container extending along an axial length and having opposed first and second ends, the first end comprising a downstream opening for dispensing the bone cement downstream from the mixing container; a mixing element movably disposed within the mixing container; and a plunger comprising a piston movably disposed within the mixing container. In this system. with a first coupling, the mixing element moves by assistance of a motor along the axial length of the mixing container without translation of the plunger to mix the bone cement. In this system. with a second coupling, the mixing element and plunger are driven together along the axial length of the mixing container.

18 Claims, 12 Drawing Sheets

BONE CEMENT MIXER

CROSS REFERENCE TO RELATED APPLICATIONS

This application is a continuation of U.S. Ser. No. 17/872,785 filed Jul. 25, 2022 entitled "BONE CEMENT MIXER" (the entire contents of which are incorporated herein by reference).

BACKGROUND OF THE INVENTION

Field of the Invention

The present invention is generally related to bone cement mixing and delivery systems in which components of bone cement are mixed together in a mixer to form a bone cement mixture. The mixture is transferred to a delivery device and then delivered to a target site, such as a vertebral body or other anatomical site.

Description of the Related Art

In bone fusion for example, a bone cement is then placed in at the site for fusion of the bone segments together. The bone cement ultimately fills the interstices, thereby facilitating a strong mechanical interlock between the bones. To facilitate a strong mechanical interlock, it is desirable that the bone cement is able to freely flow into the porous recesses of the bone and any surgically produced holes resulting from the surgical procedures.

As described in U.S. Pat. No. 6,020,396 (the entire contents of which are incorporated herein by reference), conventional acrylate-based bone cements are widely used by surgeons. These conventional acrylate-based bone cements are generally supplied to the surgeon as two separate components, a liquid component and a powder component. The liquid component of the bone cement generally comprises a liquid mixture with monomeric methyl methacrylate as the principal constituent. The powder component of these bone cements generally comprises a dry powder mixture with the primary constituent being a [methyl methacrylate-styrene] copolymer.

The recommended manner by which the liquid and dry components of conventional bone cements are mixed involves emptying the powdered component into a sterile container followed by addition of the liquid component. The components are then mixed thoroughly until polymerization commences. The specific mixing time depends on the bone cement used; the atmospheric conditions in the operating room, i.e., the temperature; and the method to be used to administer the bone cement. For pressurized administration, the components are mixed for a period of time before being loaded into a suitable sterile syringe while still relatively non-viscous for injection into the prepared area.

If administered before the degree of polymerization of the bone cement has proceeded to a suitable extent, the bone cement will be too fluid, difficult to handle and may cause overflow problems wherein the bone cement enters undesirable locations inside the patient where it must latter be removed to avoid complications. If administered after the degree of polymerization is too advanced, the bone cement will be too viscous and will not flow into all the interstitial areas and porous recesses of the bone to which the prosthetic implant is to be fixed. Furthermore, the bone cement may cure before the surgeon has sufficient time to properly align the bone segments.

Bone cement mixing and delivery systems are well known for mixing components of bone cement together to form a uniform bone cement mixture and then delivering that mixture to a target site. Such systems may employ a mixer having a handle for manually mixing the components. Once mixed, the mixture is then manually transferred to a delivery device such as a syringe. The syringe is used to inject the mixture into the target site. Examples of target sites include medullary canals for total hip arthroplasty procedures, vertebral bodies for vertebroplasty or kyphoplasty procedures, and other sites in which bone cement is required.

U.S. Pat. No. 7,371,241 (the entire contents of which are incorporated herein by reference) describes a system and a method for percutaneous delivery of bone cement during a surgical procedure. The system of the '241 patent had a plunger assembly comprising: a shaft having a first end, a middle section, and a second end, wherein the middle section is threaded; and a handle attached to the first end of the shaft. The system of the '241 patent had a dispenser hub assembly around the shaft having a collar and a hand-grip attached to the collar, and a threaded portion formed on an interior surface of the collar. The system of the '241 patent had a hollow tube for containing the bone cement during the surgical procedure having a first end and a second end, the first end of the hollow tube adapted to be removably engaged with the threaded portion of the dispenser hub assembly. The shaft was axially displaceable through the hollow tube for controlled displacement of the bone cement through the second end of the hollow tube.

U.S. Pat. No. 9,597,138 (the entire contents of which are incorporated herein by reference) describes a bone cement mixing and delivery system which included a mixer, a delivery device, and a flexible extension tube. A connector of the '138 patent is attached to a distal end of the flexible tube. The connector included a housing, a fitting and an enlarged knob. A cannula of the '138 patent was connected to the mixing and delivery system by placing the cannula fitting adjacent the connector fitting.

Other systems may employ a motorized mixer such as described in U.S. Pat. No. 7,658,537 (the entire contents of which are incorporated herein by reference). In the '537 patent, a bone cement mixing and delivery system was provided in which separate components of bone cement were mixed together in a mixer to form a bone cement mixture. The mixer of the '537 patent included a mixing paddle and a mixing shaft connected to the mixing paddle. A motor of the '537 patent operatively engaged the mixing shaft to rotate the mixing shaft and the mixing paddle to mix the components in a mixing chamber. The motor also operatively engaged a transfer mechanism. After a predetermined mixing period elapsed, the motor of the '537 patent automatically actuated the transfer mechanism to transfer the mixture to a delivery device.

U.S. Pat. No. 8,172,456 (the entire contents of which are incorporated herein by reference) describes a bone cement mixing and delivery system which included a motorized mixer and a delivery device. The mixer of the '456 patent included a paddle for mixing the components and a piston that pushed the mixed cement into the attached delivery device. The delivery device of the '456 patent included a tube into which the bone cement was forced from the mixer, and a plunger that forced the cement out of the tube during the medical procedure. The tube included an entry port through which cement is introduced into the tube from the mixer. In the 456 patent, a one-way valve attached to the tube permitted the cement to flow from the mixer through the entry port.

While these prior art systems are suitable for mixing and delivery bone cement components, there is still a need for improved bone cement mixing and delivery systems that provide greater control of mixing and delivery of the mixed bone cement to a target site in a patient.

SUMMARY OF THE INVENTION

In one embodiment, there is provided a bone cement mixing and dispensing system for mixing and delivering bone cement therefrom. The system has a mixing container for holding a bone cement mixture, the mixing container extending along an axial length and having opposed first and second ends, the first end comprising a downstream opening for dispensing the bone cement downstream from the mixing container; a mixing element movably disposed within the mixing container; and a plunger comprising a piston movably disposed within the mixing container. In this system. with a first coupling, the mixing element moves by assistance of a motor along the axial length of the mixing container without translation of the plunger to mix the bone cement. In this system. with a second coupling, the mixing element and plunger are driven together along the axial length of the mixing container.

In one embodiment, there is provided a method for bone cement mixing and dispensing. The method mixes a bone cement mixture by a motor driving a mixing element along an interior of an inclined mixing tube, primes the bone cement mixture to remove extraneous air therefrom, detaches the mixing tube from a stand supporting the motor; and expels the bone cement mixture from mixing tube.

In one embodiment, there is provided a mixing paddle. The mixing paddle is included in a bone cement mixing and dispensing system. The paddle is drivable along an axial length of a mixing container holding a bone cement mixture; the paddle is attached to a piston movably disposed within the mixing container, and the paddle is a) with a first coupling state, not coupled to a mixing element and b) with a second coupling state, coupled to the mixing element so that the mixing element and the paddle drive together along the axial length of the mixing container.

In one embodiment, there is provided a bone cement mixing and dispensing system for mixing and delivering bone cement therefrom. The system has a mixing container for holding a bone cement mixture, with the mixing container extending along an axial length and having opposed first and second ends, the first end comprising a downstream opening for dispensing the bone cement from the mixing container. The system has a mixing element movably disposed within the mixing container and coupled to a drive shaft for rotating the mixing element, and a plunger comprising a piston movably disposed within the mixing container. In this system, the drive shaft passes axially through a bore in the piston.

In one embodiment, there is provided a method for bone cement mixing and dispensing. The method mixes a bone cement mixture by a drive shaft driving a mixing element along an interior of a mixing container, wherein the drive shaft passes through a bore in a piston of a plunger. The method primes the bone cement with the plunger mixture to remove extraneous air therefrom, and expels the bone cement mixture from the mixing container.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE INVENTION

A bone cement mixer in general has a mixing container (referred to herein as a "mixing tube" but not necessarily restricted to a tubular shape) in which powder component is mixed along with a liquid component to form a bone cement mixture. A bone cement mixer in general has mixing means which may be motorized or operated manually in order to mix the powder and liquid components in the mixing container to form a mixed bone cement mixture. A bone cement mixer in general has an expulsion means for expelling the mixed bone cement mixture from the mixing container.

Figure 1:
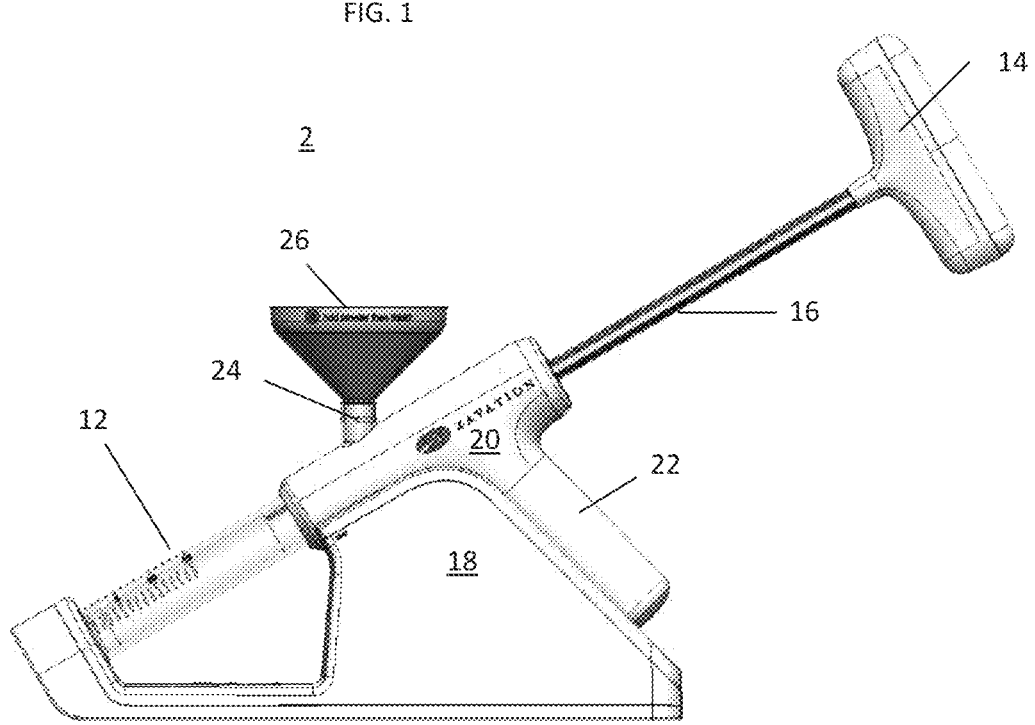
FIG. 1 is a view of the bone cement mixing and dispensing system showing various embodiments of the present invention.

FIG. 1 shows elements of the bone cement mixing and dispensing system according to various embodiments of the present invention. The bone cement mixing and dispensing system 2 shown in FIG. 1 includes a mixing tube 12 for containing and mixing bone cement therein. The mixing tube 12 extends along an axial length and has opposed first and second ends, the first end having a downstream opening 12a (best seen in FIG. 7) for dispensing the bone cement downstream from the mixing tube. The bone cement mixing and dispensing system 2 includes a fill opening 24 and fill funnel 26 (which may be integrated into a single unit) for providing the bone cement components to be mixed into mixing tube 12.

Commercially available bone cement (useable in the present invention) typically is available as acrylic bone cement (low, medium or high viscosity polymethyl methacrylate (PMMA)), calcium phosphate cement (CPC) and glass polyalkenoate (ionomer) cement (GPC). Suppliers of commercial bone cement include Heraeus Holding, DJO Global, Stryker, Zimmer Biomet, TEKNIMED, Tecres, Smith & Nephew, 3M, Exactech, Inc., DePuy Synthes Companies, Orthofix International N.V., and BSN medical GmbH.

The bone cement components (useable in the present invention) may include, as noted above, conventional acrylate-based bone cements supplied as two separate components, a liquid component and a powder component. The liquid component of the bone cement generally comprises a liquid mixture with monomeric methyl methacrylate as the principal constituent. The liquid component may include (a) at least 50% of monomeric methacrylate, up to 5% of a tertiary amine and between 10% and 45% of at least one C2-C6 alkyl methacrylate, (b) a powder component including polymethylmethacrylate, and (c) a catalytic system such as one including dimethyl-p-toluidine. The powder component of these bone cements generally comprises for example calcium hydroxide particles with the primary constituent being a [methyl methacrylate-styrene] copolymer. Further, as in the '396 patent noted above, small amounts of poly(butyl methacrylate can be added to the acrylate based bone cements to improve the fatigue strength of conventional acrylate based bone cements. For example, as detailed in the '396 patent and useable in the present invention, a small amount of the dry powder component of a conventional acrylate based bone cement can be replaced with poly(butyl methacrylate) powder prior to mixing resulting in a dry powder component comprising no more than 5 wt % poly(butyl methacrylate), preferably no more than 1 wt %, most preferably less than 1 wt %.

Besides these components, the bone cement components used in the present invention may include antibiotics such as described in U.S. Pat. No. 5,968,999 (the entire contents of which are incorporated herein by reference). The bone cement components used in the present invention may also include, as detailed in U.S. Pat. No. 9,713,654 (the entire contents of which are incorporated herein by reference), a radiolucency component such as a radiolucent particle of barium sulfate or zirconium dioxide coated with titanium oxide added to a bone cement composition.

Returning back to FIG. 1, the bone cement mixing and dispensing system 2 further includes a plunger handle 14 (to be used after the bone cement has been mixed) to expel the bone cement from the mixing tube 12 by way of pushing a plunger (shown in later views) inside the mixing tube toward the downstream opening. A lead screw 16 connects the handle to the plunger. The plunger and other gear components are contained in plunger housing 20. The plunger housing 20 is detachable from motor housing 18, permitting the plunger 14, plunger housing 20 (including housing handle 22), and the mixing tube 12 to be moved as a portable unit close to a patient in need of the bone cement.

Figure 2:
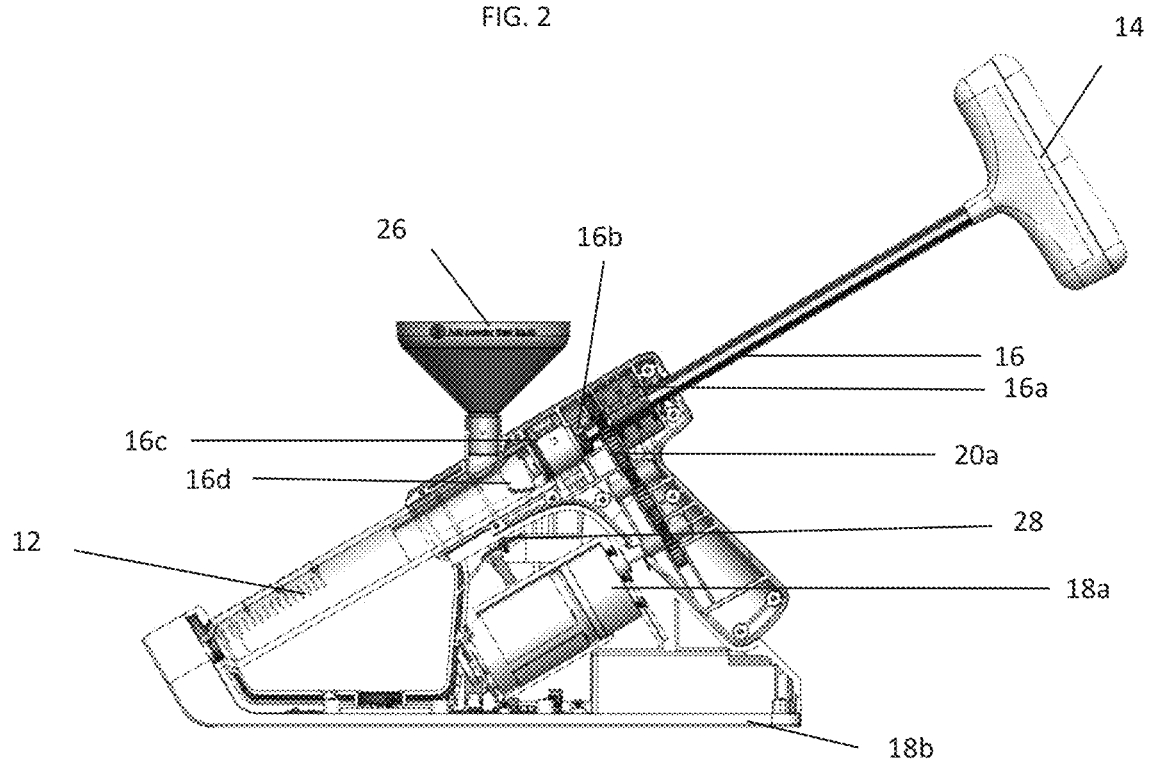
FIG. 2 is a cut-out view of the bone cement mixing and dispensing system showing various embodiments of the present invention.
Figure 3:
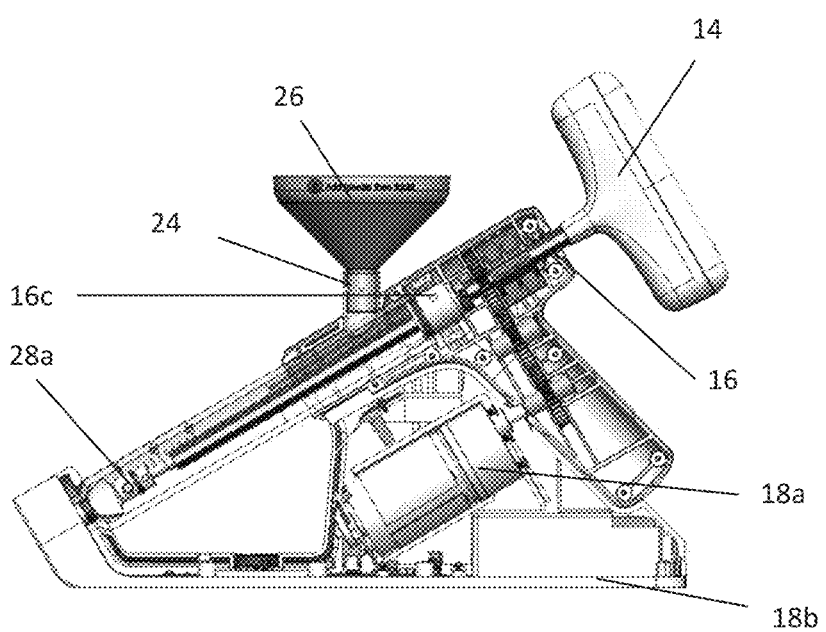
FIG. 3 is a cut-out view of the bone cement mixing and dispensing system showing the arrangement of the system components in a distal/mix position.

As shown in FIG. 2, drive coupling 16b couples the mixing element 16d to gear train 20a connected to motor 18a. Motor housing 18 houses motor 18a such as a DC motor having an encoder used to track the speed of the motor and indirectly the advancement of a mixing element such as mixing paddle 16d along the axial length of mixing tube 12. A Hall Effect Sensor 28 may be utilized to track the position of magnet 28a attached to mixing paddle 16d (as shown in FIG. 3). As shown in FIG. 2, a stand 18b supports motor 18a and motor housing 18, and further serves to support the other components shown in the drawings above motor housing 18. As shown in the drawings, stand 18b and motor housing 18 mount mixing tube 12 at an angle offset from vertical and offset horizontal. In one embodiment of the present invention, the angle offset from horizontal can vary from 10° to 85° (and every angle in between) or can vary from 30° to (and every angle in between). By having this offset angle, the mixing of the bone cement is facilitated by gravity which makes the mixture collapse upon itself especially in view of the design of mixing paddle 16d which is that of a helical paddle.

As seen from FIGS. 1-3, plunger 16c may comprise a piston which is movably disposed within mixing tube 12. Plunger housing 20 is attached to the second end of mixing tube 12 for receiving the plunger in a retracted position. In one embodiment of the present invention, mixing paddle 16d can travel along the axial length of the mixing tube with plunger 16c remaining stationary, as illustrated by FIG. 3.

The delivery handle components (including mixing tube, paddle, piston, etc.) may be comprised of various plastic resins, and can be formed for example by an injection molding process. The plastic resins may be chosen based on mechanical properties (to withstand high pressures inside mixing tube), chemical properties (plastics compatible and not reactive with the bone cement components) and optical properties (optionally transparency for the mixing tube important to assist the operator). Examples of useful plastic resins include but are not limited to include Acetal, Nylon, Teflon, and Polyester. All components within the delivery handle have the potential to contact the bone cement. Components in primary contact with cement include the mixing tube, paddle, piston, leadscrew, o-rings and coupling. Typically, the components for the delivery handle components are disposable for a one-time use.

In the one embodiment of the present invention, the mixing paddle (or parts thereof) can be made from rigid plastic. In another embodiment, the mixing paddle (or parts thereof) can be made from a flexible elastomer. In still another embodiment, the mixing paddle is rigid enough to mix cement while also being flexible enough to compress/collapse at the distal end of the mixing tube, minimizing cement loss.

Rotational and translational speed are based on total mixing time as well as volume of delivery per full rotation. One design input for example may require that a volume of 0.50 cc of cement be dispensed with a single rotation of the T-handle. Given the mixing tube inner diameter of about 20 mm, a screw pitch of 0.0246 threads per cm may achieve this requirement.

Secondarily, the mixing cycle preferably, but not necessarily, completes within a range of seconds. Given the screw pitch of 0.0246 threads per cm, a mixing tube length of 15 cm, and six (6) required passes along the length of the mixing tube can complete the mixing. A rotational speed of 350 rpm is typical, but the present invention is not so limited.

In one embodiment of the present invention, the helical pattern of mixing paddle 16d improves mixing homogeneity. The helical geometry induces movement of cement mixture both forward and behind the mixing paddle. A clearance between the outside perimeter of the helical paddle and the inside wall of the mixing tube facilitates the mixing action. This attribute expedites comingling of the liquid and powder components as well as preventing compaction of cement at the distal end of the mixing tube during the first mixing pass. The present invention is not limited to the shape/design of the mixing paddle 16d shown in the drawings and may include other helical designs such as a helical coil, a helical spiral, a helical ribbon, a helical wire, etc. For any of the helical shapes described herein, the distal end of the mixing paddle may be composed of a flexible/collapsible material, facilitating the expulsion of the mixed bone cement from mixing tube 12.

Figure 4:
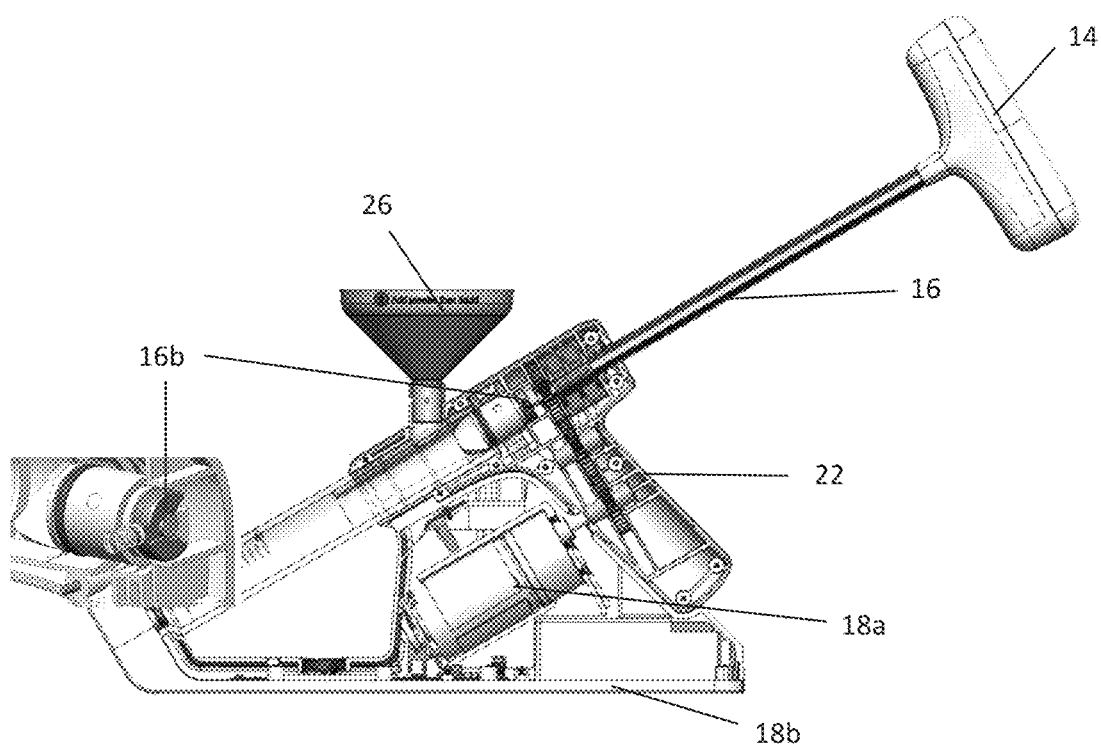
FIG. 4 is a cut-out view of the bone cement mixing and dispensing system showing the arrangement of the system components for coupling to the plunger.

FIG. 4 is a cut-out view of the bone cement mixing and dispensing system showing the arrangement of the system components for coupling to the plunger. When the plunger 16c is not coupled to the leadscrew 16, rotation of the leadscrew 16 by handle 14 or by geartrain 20a results in the leadscrew merely turning inside a bore of plunger 16c with no (or only limited) motion coupled to plunger 16c. Once the mixing is complete, drive coupling 16b couples the leadscrew 16 to plunger 16c and rotation of leadscrew 16 now advances plunger 16c, mixing paddle 16d, and leadscrew 16 together along the axial direction. In one embodiment of the present invention, the mixing paddle 16d continues to rotate while plunger 16c is pushing against bone cement mixture.

Figure 5A:
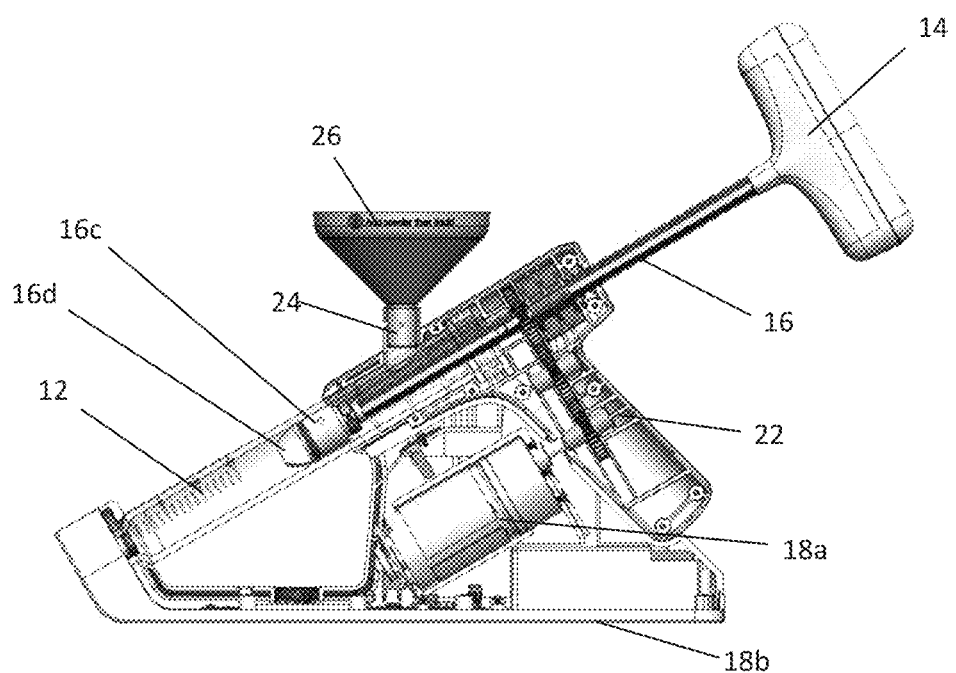
FIG. 5A is a cut-out view of the bone cement mixing and dispensing system showing the arrangement of the system components in an air purge position.

As shown in the inset of FIG. 4, to couple plunger 16c to leadscrew 16, the leadscrew is positioned to where a machined shoulder in leadscrew 16 is aligned with drive coupling 16b. Once in alignment, drive coupling 16b is pushed inwardly across the machined shoulder on the leadscrew 16 to mechanically couple plunger 16c to the leadscrew 16. With the drive coupling 16b mechanically coupled to the plunger 16c and to the leadscrew 16, advancement of the leadscrew 16 along the axial direction pushes the plunger 16c and the mixing paddle 16d together in the axial direction (as shown in FIG. 5A). The spring biases drive coupling 16b against the leadscrew. When the shoulder on the leadscrew is exposed, drive coupling 16b can be pushed into position.

Figure 5B:
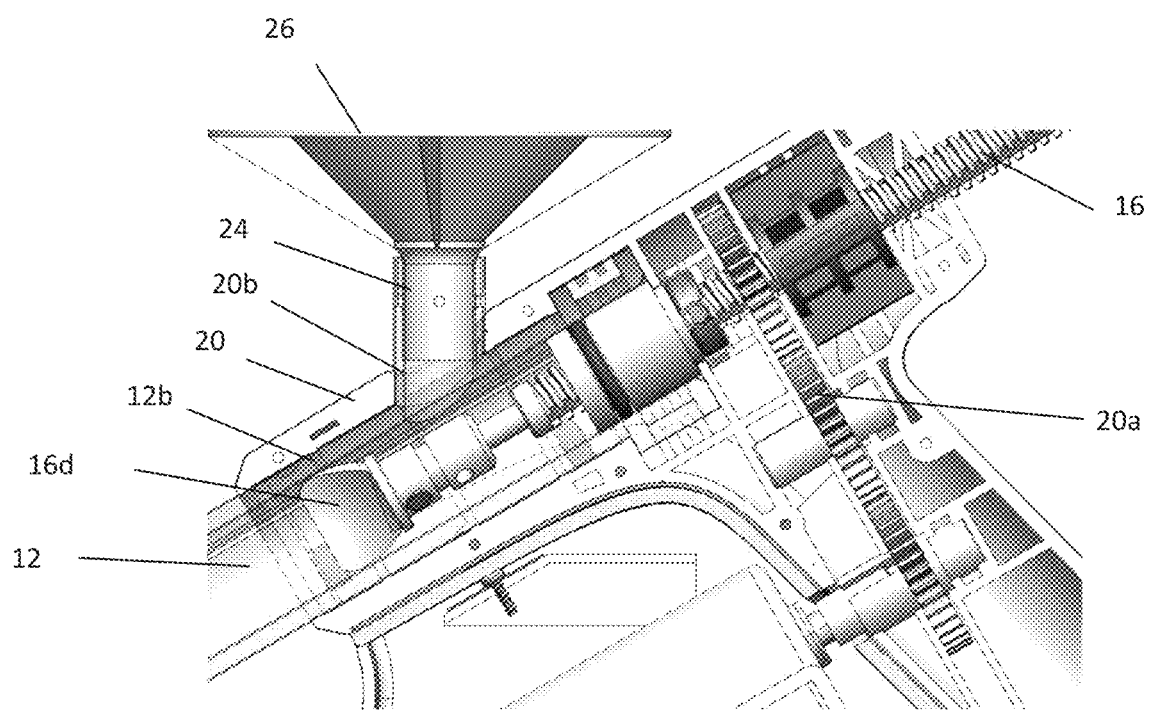
FIG. 5B is an expanded cut-out view of the bone cement mixing and dispensing system showing the arrangement of the system components in the air purge position.

More specifically, FIG. 5A is a cut-out view of the bone cement mixing and dispensing system showing the system arrangement of the system components in an air purge position. In one embodiment of the present invention, once the bone cement has been mixed, the mixture can be primed to remove extraneous air from the mixture. In this process, the plunger 16c pushes against the bone cement mixture at positions along the axial length of mixing tube 12 where the mixture is open to vent 24. As illustrated in FIG. 5A, paddle 16d moving with plunger 16c may travel substantially beyond vent 24 to push on the bone cement mixture. Air trapped in the mixture may be communicated through groove 12b (shown in the view of FIG. 5B) and communicated into port 20b for venting through opening 24. Preferably, but not necessarily, groove 12b is at the top upright position in the mixing tube 12. The forcing of trapped air from the mixed bone cement mixture, when both the plunger 16c and paddle 16c move toward the distal end of mixing tube 12, will be referred to herein as "priming" the mixture. During priming, the downstream opening of mixing tube 12 is occluded by fitting into a far end of stand 18b.

Figure 6:
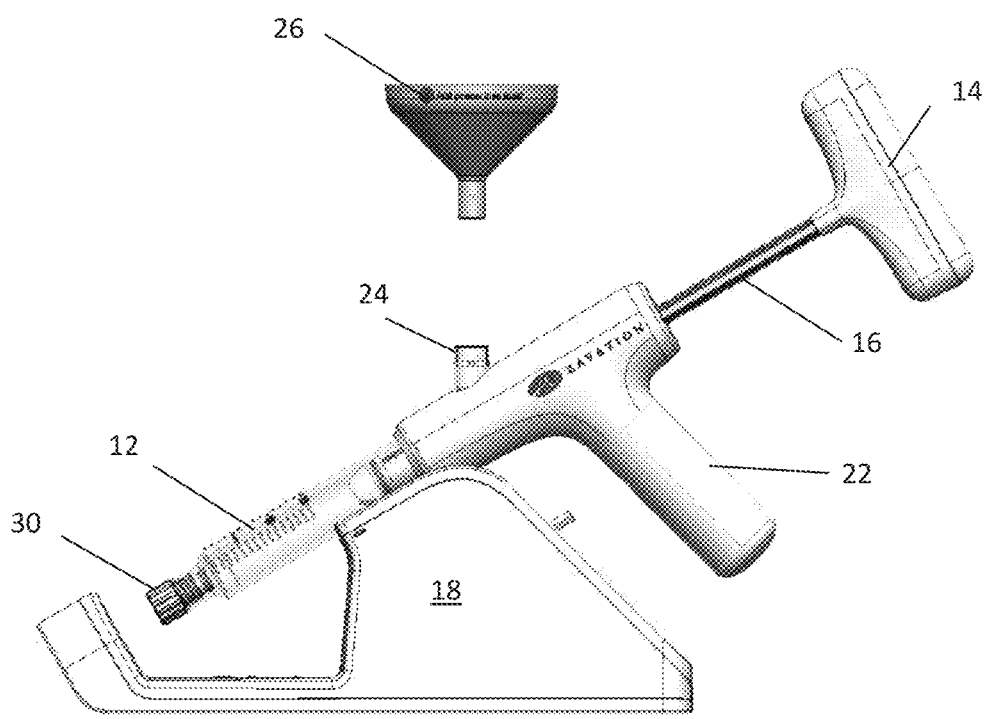
FIG. 6 is a view of the bone cement mixing and dispensing system showing the system components prior to delivery of the bone cement from the mixing tube.

Once the mixture is primed, the plunger housing 20 can be unlocked from the motor housing 18. FIG. 6 is a view of the bone cement mixing and dispensing system showing the system components prior to delivery of the bone cement from the mixing tube. Turning leadscrew 16 through stationary leadscrew nut 16a drives plunger 16c along the axial length of mixing tube 12.

Figure 7:
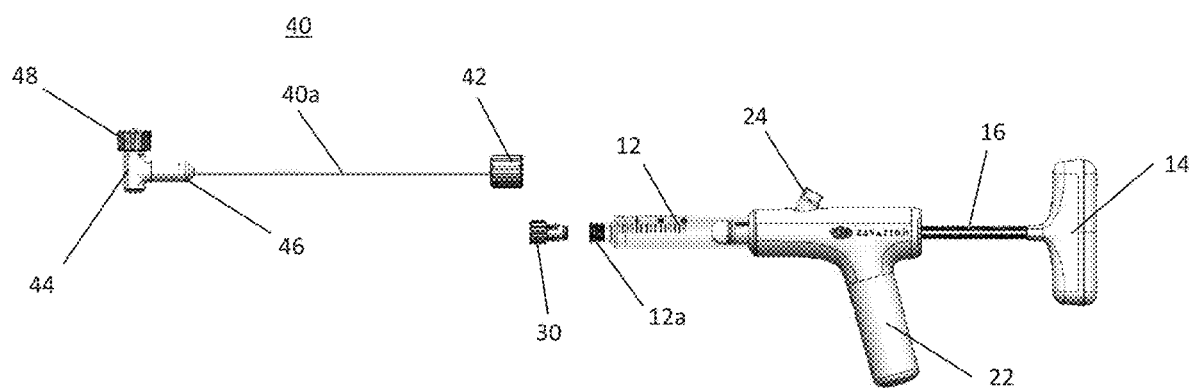
FIG. 7 is a view of the detached bone cement dispenser including the system components for delivery of the mixed bone cement from the detached mixing tube to a dispenser.

As seen in FIG. 6, a fitting 30 is used to prevent the bone cement mixture from leaking from the mixing tube 12 before being attached to a dispenser (such as dispenser 40 shown in FIG. 7). Fitting 30 could be a plug, a valve, or a transition piece with complementary fittings for coupling between the downstream opening 12a and dispenser 40.

Dispenser 40 shown in FIG. 7 includes a dispenser tube 40a, an input coupling 42 for connecting dispenser tube 40a to downstream opening 12a or to fitting 30. Dispenser 40 also includes a capillary coupler 44 for connecting dispenser tube 40a to a capillary for delivery of the bone cement to a patient site. The capillary coupler 44 includes a dispenser tube coupler 46 and a capillary tube coupler 48. Capillary tube coupler 48 may include a knob whose rotation compresses seals on an outside diameter of a capillary tube to both seal and hold the capillary tube to the capillary coupler 44.

Figure 8:
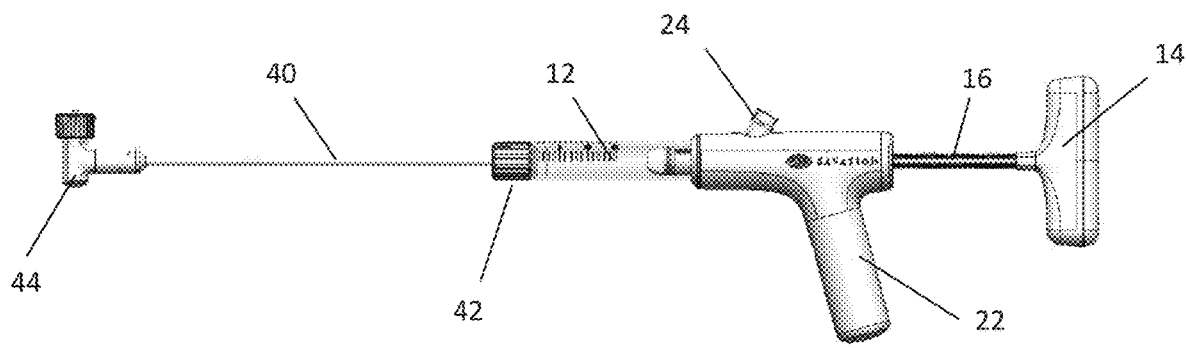
FIG. 8 is a view of the detached bone cement dispenser.

FIG. 8 is a view of the detached bone cement dispenser. Turning of handle 14 rotates lead screw 16 which forces plunger 16 to push the bone cement mixture out of downstream opening 12a in mixing tube 12, though dispenser 40, and into a capillary where the bone cement will be delivered to a patient site.

Figure 9:
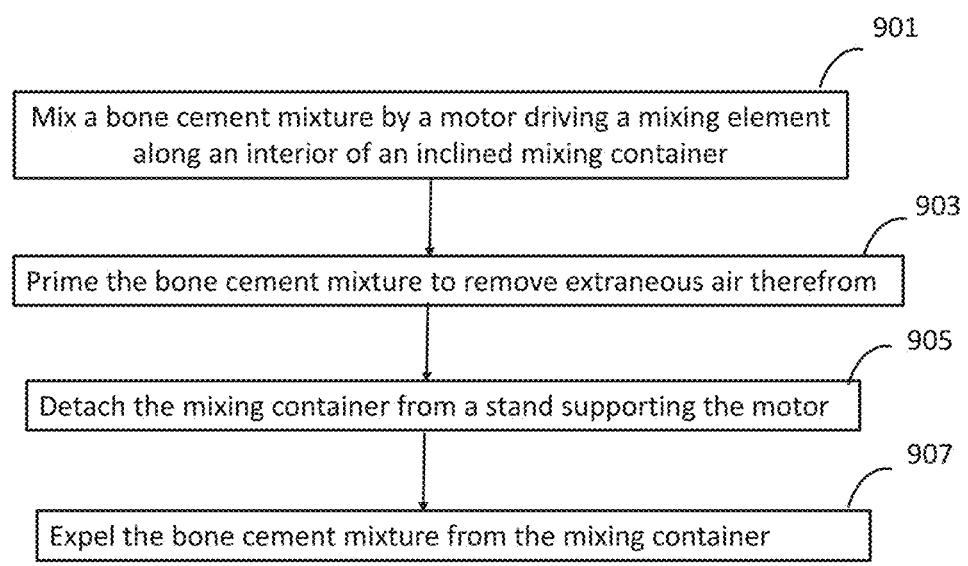
FIG. 9 is a flowchart depicting a method of the present invention for bone cement mixing and dispensing.

FIG. 9 is a flowchart depicting a method of the present invention for mixing and delivery of bone cement to a patient site. As shown in FIG. 9, at 901, a bone cement mixture is mixed by a motor driving a mixing element along an interior of an inclined mixing container (e.g., a mixing tube). At 903, the bone cement mixture is primed to remove extraneous air from the bone cement mixture. At 905, the mixing container is detached from a stand supporting the motor. At 907, the bone cement mixture is expelled from the mixing container for delivery to a patient site.

Figure 10:
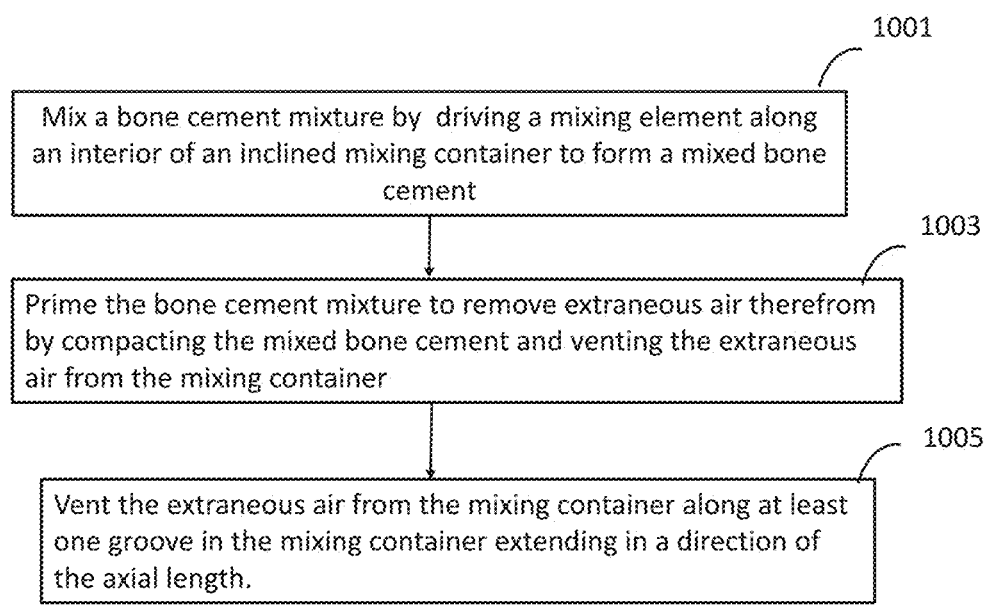
FIG. 10 is a flowchart depicting a method of the present invention for bone cement mixing and priming.

FIG. 10 is a flowchart depicting a method of the present invention for bone cement mixing and priming. As shown in FIG. 10, at 1001, a bone cement mixture is mixed by driving a mixing element along an interior of an inclined mixing container to form a mixed bone cement. At 1003, the mixed bone cement mixture is primed to remove extraneous air therefrom by compacting the mixed bone cement and venting the extraneous air from the mixing container. At 1005, the extraneous air is vented along at least one groove in the mixing container extending in a direction of the axial length.

Figure 11:
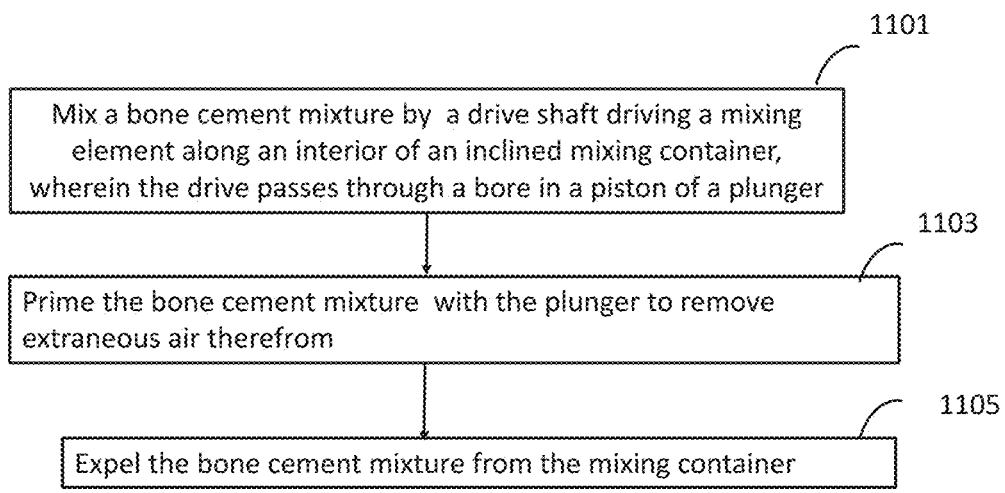
FIG. 11 is a flowchart depicting another method of the present invention for bone cement mixing and dispensing.

FIG. 11 is a flowchart depicting another method of the present invention for bone cement mixing and dispensing. As shown in FIG. 11, at 1101, a bone cement mixture is mixed by drive shaft (for example a leadscrew) driving a mixing element along an interior of a mixing container, wherein the drive shaft passes through a bore in a piston of a plunger. At 1103, the bone cement mixture is primed to remove extraneous air from the bone cement mixture. At 1105, the bone cement mixture is expelled from the mixing container for delivery to a patient site.

In the embodiments described above, any of the components and instruments described may be used individually as part of the invention and need not to be assembled as shown in the drawings. Furthermore, while the following statements and claims describe various aspects of the invention, the invention is not limited to those aspects alone as many of the described elements above individually or in combination with other elements shown define unique features especially in the context of bone cement mixing and delivery.

STATEMENTS OF THE INVENTION

The following numbered statements of the present invention represent various aspects of the invention.

1. A bone cement mixing and dispensing system for mixing and delivering bone cement therefrom, the system comprising: a mixing container for holding a bone cement mixture, the mixing container extending along an axial length and having opposed first and second ends, the first end comprising a downstream opening for dispensing the bone cement from the mixing container; a mixing element movably disposed within the mixing container; a plunger comprising a piston movably disposed within the mixing container; and optionally a plunger housing attached to the second end of the mixing container for receiving the plunger in a retracted position, wherein a) with a first coupling, the mixing element moves by assistance of a motor along the axial length of the mixing container without translation of the plunger to mix the bone cement, and b) with a second coupling, the mixing element and plunger are driven together along the axial length of the mixing container.

2. The system of statement 1, wherein the mixing element is coupled to a drive shaft coupled to the motor for rotating the mixing element, and the drive shaft passes axially through a bore in the piston.

3. The system of statement 1, further comprising: a handle attached to a lead screw which, with the second coupling, manually drives the mixing element and plunger along the axial length of the mixing container.

4. The system of any of the statements above 1, wherein the mixing element is a rotatable helical-shaped paddle.

5. The system of any of the statements above, wherein the mixing element is a collapsible element.

6. The system of any of the statements above, further comprising a port on the plunger housing for supply of bone cement components to the mixing container.

7. The system of any of the statements above, wherein the port provides a vent opening for priming the bone cement mixture.

8. The system of any of the statements above, further comprising a dispenser coupled to the downstream opening of the mixing container.

9. The system of any of the statements above, wherein the dispenser includes a cannula coupling for connection to a cannula for delivery of the bone cement mixture to a patient site.

10. The system of any of the statements above, wherein the cannula coupling comprises a rotatable knob where rotation of the knob seals the cannula coupling to the cannula.

11. The system of any of the statements above, further comprising an electric motor and controls for driving at least one of the plunger and the mixing element.

12. The system of any of the statements above, wherein the controls include a Hall sensor and the mixing element includes a magnet for the Hall sensor.

13. The system of any of the statements above, wherein, with the first coupling, the controls using the Hall sensor are configured to control positioning of the mixing element along an entire travel of the mixing element along the axial length of the mixing container.

14. The system of any of the statements above, wherein, with the second coupling the controls using the Hall sensor are configured to control a position of the plunger relative to a port in the plunger housing providing a vent for priming the bone cement mixture.

15. The system of any of the statements above, further comprising a stand for holding the electric motor and the mixing container.

16. The system of any of the statements above, wherein the mixing container is detachable from the stand and thereby configured to be moveable to a place for delivery of the bone cement to a patient.

17. The system of any of the statements above, wherein the stand is configured to incline the mixing container at an angle offset from vertical and offset horizontal.

18. The system of any of the statements above, wherein the mixing container comprises an inclined mixing container held at an angle offset from horizontal from 10° to 85°.

19. The system of any of the statements above, wherein the mixing container comprises an inclined mixing container held at an angle offset from horizontal from 30° to 60°.

20. The system of any of the statements above, wherein the mixing container comprises an inclined mixing container having an interior surface and having at least one groove extending in a direction of the axial length to permit air escape from the inclined mixing container 21. The system of any of the statements above, wherein the at least one groove is disposed at or toward an upright side of the inclined mixing container.

22. A method for bone cement mixing and dispensing, comprising: mixing a bone cement mixture by a motor driving a mixing element along an interior of an inclined mixing container; priming the bone cement mixture to remove extraneous air therefrom; detaching the mixing container from a stand supporting the motor; and expelling the bone cement mixture from the mixing container.

23. The method of statement 22, wherein a handle attached to a lead screw manually drives the mixing element and plunger along the axial length of the mixing container.

24. The method of any of the statements 22 and following, wherein the mixing element is rotatably and axially movable within the mixing container in order to mix the bone cement along the entirety of the mixing container.

25. The method of any of the statements 22 and following, wherein the mixing element is a rotatable helical-shaped paddle.

26. The method of any of the statements 22 and following, wherein the mixing element is a collapsible element.

27. The method of any of the statements 22 and following, wherein a port on the plunger housing supplies bone cement components to the mixing container.

28. The method of any of the statements 22 and following, wherein the port provides a vent opening for priming the bone cement mixture.

29. The method of any of the statements 22 and following, wherein a dispenser coupled to the downstream opening of the mixing container.

30. The method of any of the statements 22 and following, wherein the dispenser includes a cannula coupling for connection to a cannula for delivery of the bone cement mixture to a patient site.

40. The method of any of the statements 22 and following, wherein the cannula coupling comprises a rotatable knob where rotation of the knob seals the cannula coupling to the cannula.

42. The method of any of the statements 22 and following, wherein an electric motor and controls drive at least one of the plunger and the mixing element.

43. The method of any of the statements 22 and following, wherein the controls include a Hall sensor and the mixing element includes a magnet for the Hall sensor.

44. The method of any of the statements 22 and following, wherein the controls using the Hall sensor control positioning of the mixing element along an entire travel of the mixing element along the axial length of the mixing container.

45. The method of any of the statements 22 and following, wherein the controls using the Hall sensor control a position of the plunger relative to a port in the plunger housing providing a vent for priming the bone cement mixture.

46. The method of any of the statements 22 and following, wherein a stand holds the electric motor and the mixing container.

47. The method of any of the statements 22 and following, wherein the mixing container is detachable from the stand and thereby moveable to a place for delivery of the bone cement to a patient.

48. The method of any of the statements 22 and following, wherein the stand is configured to incline the mixing container at an angle offset from vertical and offset horizontal.

49. The method of any of the statements 22 and following, wherein the mixing container is inclined at an angle offset from horizontal from 10° to 85°.

50. The method of any of the statements 22 and following, wherein the mixing container is inclined at an angle offset from horizontal from 30° to 60°.

51. The method of any of the statements 22 and following, wherein the mixing container comprises an inclined mixing container having an interior surface and having at least one groove extending in a direction of the axial length to permit air escape from the inclined mixing container.

53. The method of any of the statements 22 and following, wherein the at least one groove is disposed at or toward an upright side of the inclined mixing container.

56. A system for mixing and priming a bone cement, the system comprising:
an inclined mixing container for holding a bone cement mixture, the mixing container extending along an axial length and having opposed first and second ends, the first end comprising a downstream opening for dispensing the bone cement downstream from the mixing container; a mixing element movably disposed within the mixing container; a plunger comprising a piston movably disposed within the mixing container; and optionally a plunger housing attached to the second end of the mixing container for receiving the plunger in a retracted position, wherein the mixing container comprises an interior surface and having at least one groove extending in a direction of the axial length to permit air escape to a vent for the mixing container, and the at least one groove is disposed at or toward an upright side of the inclined mixing container.

57. The system of statement 56 including any of the aspects of the bone cement mixing and dispensing system set forth in statements 2-21.

58. A method for mixing and priming a bone cement, comprising: mixing a bone cement mixture by driving a mixing element along an interior of an inclined mixing container to form a mixed bone cement; and priming the mixed bone cement mixture to remove extraneous air therefrom by compacting the mixed bone cement and venting the extraneous air from the mixing container along at least one groove extending in a direction of the axial length, wherein the at least one groove is disposed at or toward an upright side of the inclined mixing container.

59. The method of statement 58 including any of the aspects of the method for bone cement mixing and dispensing set forth in statements 22-53

60. A mixing paddle comprising: a paddle included in a bone cement mixing and dispensing system, wherein
the paddle is drivable along an axial length of a mixing container holding a bone cement mixture to mix the bone cement mixture, and
the paddle is a) with a first coupling state, not coupled to a plunger used to expel bone cement from the mixing container and b) with a second coupling state, coupled to the plunger so that the plunger and the paddle drive together along the axial length of the mixing container.

61. The paddle of statement 60 including any of the aspects of the bone cement mixing and dispensing system set forth in statements 2-21.

62. A bone cement mixing and dispensing system for mixing and delivering bone cement therefrom, the system comprising: a mixing container for holding a bone cement mixture, the mixing container extending along an axial length and having opposed first and second ends, the first end comprising a downstream opening for dispensing the bone cement from the mixing container; a mixing element movably disposed within the mixing container and coupled to a drive shaft (optionally coupled to a motor) for rotating the mixing element; a plunger comprising a piston movably disposed within the mixing container; and optionally a plunger housing attached to the second end of the mixing container for receiving the plunger in a retracted position, wherein the drive shaft passes axially through a bore in the piston.

63. The system of statement 62 including any of the aspects of the bone cement mixing and dispensing system set forth in statements 2-21.

64. A method for bone cement mixing and dispensing, comprising: mixing a bone cement mixture by a drive shaft driving a mixing element along an interior of a mixing container, wherein the drive shaft passes through a bore in a piston of a plunger; priming the bone cement mixture to remove extraneous air therefrom; and expelling the bone cement mixture from the mixing container.

65. The method of statement 64 including any of the aspects of the method for bone cement mixing and dispensing set forth in statements 22-53.

Numerous modifications and variations of the present invention are possible in light of the above teachings. It is therefore to be understood that within the scope of the appended claims, the invention may be practiced otherwise than as specifically described herein.

The invention claimed is:

1. A bone cement mixing and dispensing system for mixing and delivering bone cement therefrom, the system comprising:
a mixing container for holding a bone cement mixture, the mixing container extending along an axial length and having opposed first and second ends, the first end comprising a downstream opening for dispensing the bone cement from the mixing container;
a mixing element movably disposed within the mixing container;
a plunger comprising a piston movably disposed within the mixing container
a motor for driving the mixing element along the axial length of the mixing container;
a control for the motor which controls driving of at least one of the plunger and the mixing element,
wherein
the control senses a position of the mixing element and controls positioning of the mixing element along an entire travel of the mixing element along the axial length of the mixing container by sensing a position of the mixing element.

2. The system of claim 1, wherein the control comprises a Hall sensor.

3. The system of claim 2, further comprising a port in the plunger housing providing a vent for priming the bone cement mixture, wherein the control using the Hall sensor is configured to control a position of the plunger relative to the port in the plunger housing.

4. The system of claim 1, wherein the mixing element is coupled to a drive shaft coupled to the motor for rotating the mixing element.

5. The system of claim 1, wherein the drive shaft passes axially through a bore in the piston.

6. The system of claim 1, wherein
in a first operational state, the mixing element moves, by assistance of the motor, along the axial length of the mixing container to mix the bone cement without translation of the plunger which is not coupled to the motor, and
in a second operational state, both the mixing element and plunger are coupled to the motor and driven together by the motor along the axial length of the mixing container.

7. The system of claim 1, wherein the mixing element is a rotatable paddle.

8. The system of claim 1, wherein the mixing element is a rotatable helical-shaped paddle.

9. The system of claim 1, further comprising
a port on the mixing chamber which supplies the bone cement components to the mixing container.

10. The system of claim 9, wherein the port provides a vent opening for priming the bone cement mixture.

11. The system of claim 1, further comprising a dispenser coupled to the downstream opening of the mixing container.

12. The system of claim 11, wherein the dispenser includes a cannula coupling for connection to a cannula for delivery of the bone cement mixture to a patient site.

13. The system of claim 12, wherein the cannula coupling comprises a rotatable knob where rotation of the knob seals the cannula coupling to the cannula.

14. The system of claim 1, further comprising a stand which inclines the mixing container at an angle offset from horizontal ranging from 10° to 85°.

15. The system of claim 14, wherein the angle ranges from 30° to 60°.

16. The system of claim 14, wherein the mixing container is detachable from the stand and is moveable to a place for delivery of the bone cement to a patient.

17. The system of claim 1, wherein the mixing container comprises at least one groove extending in a direction of the axial length to permit air escape from the mixing container.

18. The system of claim 17, wherein the at least one groove is disposed at or toward an upright side of the inclined mixing container.

* * * * *